United States Patent [19]

Lacroix

[11] 4,078,069

[45] Mar. 7, 1978

[54] AGRICULTURAL FUNGICIDAL COMPOSITION

[75] Inventor: Laurent Lacroix, Saint Fargeau, France

[73] Assignee: Philagro, Lyon, France

[21] Appl. No.: 711,367

[22] Filed: Aug. 3, 1976

[30] Foreign Application Priority Data

Aug. 13, 1975 France .................. 75 25210

[51] Int. Cl.² ........................ A01N 9/22
[52] U.S. Cl. ............................ 424/272
[58] Field of Search ........................ 424/272

[56] References Cited

U.S. PATENT DOCUMENTS

| | | | |
|---|---|---|---|
| 3,385,862 | 5/1968 | Metivier et al. ................ | 260/307 |
| 3,641,045 | 2/1972 | Meek ................ | 424/272 X |
| 3,876,413 | 4/1975 | Boesch ................ | 71/92 |

FOREIGN PATENT DOCUMENTS 2,413,938  9/1974  Germany.

OTHER PUBLICATIONS

Chemical Abstracts 69:52143t (1968).
Chemical Abstracts 74:100064v (1971).

Primary Examiner—Leonard Schenkman
Attorney, Agent, or Firm—Browdy and Neimark

[57] ABSTRACT

Fungicidal compositions for agricultural use, containing 3-(2,4-dichloro-5-hydroxy-phenyl)-5-tertiary butyl-1,3,4-oxadiazolin-2-one as the active material.

4 Claims, No Drawings

AGRICULTURAL FUNGICIDAL COMPOSITION

BACKGROUND AND SUMMARY

The present invention relates to new fungicidal compositions for agricultural use which contain, as the fungicidal agent, 3-(2,4-dichloro-5-hydroxy-phenyl)-5-tertiary butyl-1,3,4-oxadiazolin-2-one, in association with one or more diluents or adjuvants which are compatible therewith and can be used in agriculture.

It also relates to a process for the fungicidal treatment of plants by means of these compositions.

3-(2,4-Dichloro-5-hydroxy-phenyl)-5-tertiary butyl-1,3,4-oxadiazolin-2-one, of the general formula:

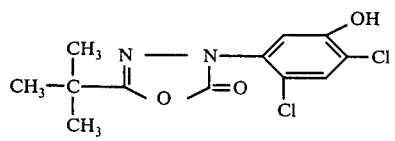

is known as an intermediate for the synthesis of herbicidal compounds. Its preparation is described especially in Belgian Pat. No. 812,654.

The fungicidal activity of 3-(2,4-dichloro-5-hydroxyphenyl)-5-tertiary butyl-1,3,4-oxadiazolin-2-one manifests itself against numerous fungi, especially against those which are phytopathogenic.

DETAILED DESCRIPTION

The examples which follow are given, without implying a limitation, respectively to illustrate the fungicidal activity of the compositions according to the invention and to describe a particular composition which can be used according to the invention.

EXAMPLE 1:

In vitro test of the fungicidal activity

For this experiment, a series of test tubes each containing an artificial culture medium (4 ml.) (Sabouraud agar) is used.

After sterilising, in an autoclave, a suspension (2 ml.) containing the active material, at various concentrations (of active material), is added to each tube.

For different species of fungi, a suspension of spores in sterile distilled water, containing $4 \times 10^6$ spores/ml. is prepared, and each tube is inoculated with this suspension (0.25 ml.). After inoculation, the tubes are kept in an oven at 25° C for nine days.

On the ninth day of culture, the percentage inhibition of the growth of each species of fungus is evaluated for various concentrations of active material. From these results, the minimum concentration of the product which causes 95 to 100% inhibition of the growth of the fungi, called the "minimum inhibitory concentration", is determined for each species of fungus. This concentration is expressed in μg. of active material per ml. of culture medium; the results observed are reported in the table which follows.

| Fungi | Minimum inhibitory concentration (μg./ml.) |
| --- | --- |
| Fusarium oxysporum | 500 |
| Saccharomyces pastorianus | 500 |
| Botrytis cinerea | 100 |
| Trichophyton mentagrophytes | 10 |
| Candida albicans | 750 |
| Penicillium digitatum | 750 |
| Aspergillus niger | 200 |
| Colletotrichum lindemuthianum | 500 |
| Erysiphe cichoracearum | 2,000 |
| Puccinia glumarum | 2,000 |

EXAMPLE 2

This example describes the preparation of a composition which can be used in agriculture for the fungicidal treatments according to the invention.

A product (10 parts) of the condensation of octylphenol with ethylene oxide, at the rate of 10 molecules of ethylene oxide per molecule of octylphenol, is added to a solution of 3-(2,4-dichloro-5-hydroxy-phenyl)-5-tertiary butyl-1,3,4-oxadiazolin-2-one (25 parts) in a mixture (65 parts) of equal parts of toluene and acetophenone. The solution obtained is used, after dilution with water at the rate of 100 cc. of this solution per 100 liters of water, to inhibit the growth and the development of the fungi.

The agricultural compositions which contain 3-(2,4-dichloro-5-hydroxy-phenyl)-5-tertiary butyl-1,3,4-oxidiazolin-2-one as the active material are particularly useful in eliminating parasitic soil fungi, such as Ustilago sp., Helminthosporium sp., Septoria sp., Fusarium sp., Rhizoctonia sp., Phoma sp., Alternaria sp., Piricularia sp.

In addition to the active material, the compositions according to the invention contain a carrier and/or a surface-active agent.

The term "carrier", in the sense of the present description, denotes an organic or inorganic, natural or synthetic material with which the active material is associated in order to facilitate its application to the plant, to the seeds or to the soil, or to facilitate its transport or its handling. The carrier can be solid (clays, natural or synthetic silicates, resins, waxes, solid fertilisers and the like) or fluid (water, alcohols, ketones, petroleum fractions, chlorinated hydrocarbons and liquefied gases).

The surface-active agent can be an emulsifier, dispersing agent or wetting agent, and each of these can be ionic or non-ionic. By way of example there may be mentioned salts of polyacrylic acids, salts of ligninsulphonic acids and condensates of ethylene oxide with fatty alcohols, fatty acids or fatty amines.

The compositions according to the invention can be prepared in the form of wettable powders, of dusting powders, of solutions, of emulsifiable concentrates, of emulsions, of suspension concentrates and of aerosols.

Depending on the form of presentation used, the content of active material of the compositions according to the invention can vary from 0.005% to 95% by weight.

The wettable powders are usually prepared so that they contain from 20 to 95% by weight of active material and they usually contain, in addition to a solid carrier, from 0 to 5% of a wetting agent, from 3 to 10% by weight of a dispersing agent and, where this is necessary, from 0 to 10% by weight of one or more stabilisers and/or other adjuvants as penetrating agents, adhesives or anti-caking agents, dyestuffs and the like.

By way of example, the following is the composition of a wettable powder, the percentages being expressed by weight:

| | |
|---|---|
| Active material (compound of Formula I) | 50% |
| Calcium lignosulphate (deflocculating agent) | 5% |
| Isopropylnaphthalenesulphonate (wetting agent) | 1% |
| Anti-caking silica | 5% |
| Kaolin filler | 39% |

The powders for the treatment of seeds or for dusting are usually prepared in the form of a dust concentrate having a composition similar to that of a wettable powder, but without dispersing agent, and they can be diluted at the use site by means of a supplementary amount of fluid carrier, so as to give a composition which can conveniently coat the seeds to be treated and which usually contains from 0.5 to 10% by weight of active material.

By way of example, the following is the composition of a powder for the treatment of seeds:

| | |
|---|---|
| Active material (compound of Formula I) | 50% |
| Naphtalene sulfonic acid, sodium salt | 1% |
| Anti-caking silica | 6% |
| Kaolin (filler) | 43% |

The emulsifiable concentrates which can be applied by spraying, after dilution with water, usually contain, in addition to the solvent and, where necessary, a co-solvent, from 10 to 50% by weight/volume of active material, from 2 to 20% by weight/volume of emulsifiers and from 0 to 20% by weight/volume of appropriate additives such as stabilisers, penetrating agents, corrosion inhibitors, and dyestuffs and adhesives.

By way of example, the following is the composition of an emulsifiable concentrate, the amounts being expressed in g./liter:

| | | |
|---|---|---|
| Active material (compound of Formula I) | | 400 g./l |
| Dodecylbenzenesulphonate | | 24 g./l |
| Nonylphenol oxyethyleneated with 10 molecules of ethylene oxide | | 16 g./l |
| Cyclohexanone | | 200 g./l |
| Aromatic solvent | q.s.p. | 1 liter |

The suspension concentrates, which can also be applied by spraying, are prepared so that a stable fluid product is obtained which does not settle out; they usually contain from 10 to 75% by weight of active material, from 0.5 to 15% by weight of surface-active agents, from 0.1 to 10% by weight of anti-sedimentation agents such as protective colloids and thixotropic agents, from 0 to 10% by weight of appropriate additives, such as anti-foam agents, corrosion inhibitors, stabilisers, penetrating agents and adhesives, and, as the carrier, water or an organic liquid in which the active material is essentially insoluble; certain organic solid materials or inorganic salts can be dissolved in the carrier to assist in preventing the sedimentation or to act as anti-freeze agents for the water.

The aqueous dispersions or emulsions, for example the compositions obtained by diluting a wettable powder or an emulsifiable concentrate according to the invention with water, at the rate of 10 to 500 g. of active material per hectoliter of water, are also included within the general scope of the present invention. These emulsions can be of the water-in-oil type or of the oil-in-water type and they can have a thick consistency such as that of a "mayonnaise".

For so-called "ultra-low volume" application with a spray of very fine droplets, solutions in organic solvents which contain from 70 to 95% of active material are prepared.

The compositions according to the invention can contain other ingredients, for example protective colloids, adhesives or thickeners, thixotropic agents, stabilisers or sequestering agents, as well as other known active materials having pesticidal properties, in particular insecticides or fungicides.

The compositions according to the invention can be applied by any means usually employed in agriculture. Generally, good results are obtained if these compositions are used by spraying the soil at the rate of 0.5 to 5 kg. of active material per hectare.

It will be obvious to those skilled in the art that various changes may be made without departing from the scope of the invention and the invention is not to be considered limited to what is described in the specification.

What is claimed is:

1. A process for controlling fungi on plants, comprising applying to said plants
   a fungicidal composition consisting essentially of, as the active material, a fungicidally-effective amount of 3-(2,4-dichloro-5-hydroxy-phenyl)-5-tertiary butyl-1,3,4-oxadiazolin-2-one of the formula:

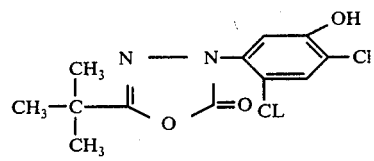

in association with at least one agricultural carrier and a surface-active agent for agricultural use and compatible with the said compound.

2. A process according to claim 1, characterized in that the dose of active material applied is between 0.5 kg./hectare and 5 kg./hectare.

3. A process for controlling fungi on plants, comprising contacting said plants with a fungicidally-effective amount of 3-(2,4-dichloro-5-hydroxy-phenyl)-5-tert. butyl-1,3,4-oxadiazolin-2-one.

4. A process for controlling fungi on seeds, comprising contacting said seeds with a fungicidally-effective amount of 3-(2,4-dichloro-5-hydroxy-phenyl)-5-tert. butyl-1,3,4-oxadiazolin-2-one.

* * * * *